(12) United States Patent
Park et al.

(10) Patent No.: US 6,506,410 B1
(45) Date of Patent: Jan. 14, 2003

(54) SUSTAINED RELEASE MICROPARTICLE AND METHOD FOR PREPARING THE SAME

(75) Inventors: Jin Kyu Park, Seoul (KR); Mork Soon Park, Taejeon (KR); Dong Seon Kim, Taejeon (KR); Il Ho Lim, Chungcheongbuk-do (KR); Ung Kil Jee, Seoul (KR); Pyung Keun Myung, Taejeon (KR); San Beom Kim, Kunsan (KR); Goo Young Jung, Chungcheongbuk-do (KR)

(73) Assignee: Kong Kook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 09/724,724

(22) Filed: Nov. 28, 2000

(30) Foreign Application Priority Data

Jun. 28, 2000 (KR) ........................................ 2000-36178

(51) Int. Cl.[7] ............................ A61K 9/14; A61K 9/50; A01N 25/00
(52) U.S. Cl. ....................... 424/489; 424/499; 424/501; 424/502; 514/938
(58) Field of Search .................................. 424/489, 501, 424/426, 499, 502; 514/938

(56) References Cited

U.S. PATENT DOCUMENTS 4,897,268 A    1/1990  Tice et al.
5,538,739 A  * 7/1996  Bodmer et al. ............. 424/501

* cited by examiner

Primary Examiner—Thurman K. Page
Assistant Examiner—Humera N. Sheikh
(74) Attorney, Agent, or Firm—Knobbe, Martens, Olson & Bear, LLP

(57) ABSTRACT

Disclosed is a method for preparing sustained release microparticles which release a physiologically active substance for long periods of time. The sustained release microparticles are prepared through a multi-emulsion process. A drug of interest is dissolved or dispersed in each of at least two oils to give at least two primary oil phases or emulsions. Each oil phase or emulsion contains a biodegradable polymer. The least two primary oil phases or emulsions are dispersed in one aqueous phase, synchronously or in succession. From the drug-dispersed solution, the organic solvents are removed to produce microparticles. Therefore, the drugs such as leutenizing hormone releasing hormones can be continuously released in vivo for prolonged periods of time, bringing about an improvement in the therapeutic effect.

11 Claims, 7 Drawing Sheets

SUSTAINED RELEASE MICROPARTICLE AND METHOD FOR PREPARING THE SAME

BACKGROUND OF THE INVENTION

1. Field of the Invention

The invention relates to a sustained-release preparation which releases a physiologically active substance for long periods of time.

2. Description of the Prior Art

To prepare sustained release type drug delivery systems (DDS), there are usually used various methods, including coacervation, emulsion phase separation, spray drying-dependent encapsulation, and solvent evaporation in organic or water phase. Of them, the solvent evaporation in water phase is the most extensively used, which is largely divided into two techniques: W/O/W (water/oil/water) double emulsification and O/W (oil/water) simple emulsification.

The W/O/W technique is usually used for the encapsulation of water-soluble drugs such as peptides or proteins. In this technique, a water-soluble drug is dissolved in water and this aqueous layer is dispersed in an organic layer containing a biodegradable polymer, so as to give a primary emulsion (water in oil). Again, this primary emulsion is dispersed in water. The O/W technique, which is usually used to capsulate lipid-soluble drugs, can be conducted by dissolving a drug and a biodegradable polymeric excipient in an organic solvent or an inorganic solvent mixture and dispersing the solution in an aqueous phase. In both of the two, the solubility of the polymer decreases as the organic solvent is removed through extraction or evaporation in the course of dispersing an oil phase of the polymer in an aqueous phase. As a result, the polymer is solidified to form microparticles. Generally, compared with those obtained by the O/W technique, the microparticles obtained by the W/O/W technique are of a more porous structure with higher surface areas so that they are high in the initial release rate of drugs.

The release time period of such sustained release microparticles is determined largely by physical and chemical properties of polymers, compositions of solvents, and kinds and concentrations of emulsifiers. Of these determinant factors, the most important are the physical and chemical properties of polymers, including chemical compositions, molecular weights, and hydrophilicity. For example, poly (lactide-co-glycolide) (PLGA), a polymer consisting of lactide and glycolide with a different molar ratio therebetween, is degraded at low rates as the lactide is increased in molar ratio or molecular weight. In this case, polymers which are higher in lactide content or greater in molecular weight lead to longer release time periods. However, where the polymer is degraded for an extended period of time, the microparticle hardly releases its encapsulated drug in some points of the early or intermediate stage. Therefore, using one polymer in preparing sustained release microparticles able to continuously release drugs for desired periods of time (e.g., one, two, three, six months or longer) requires extensive effort and time. On account of this problem, research has been directed to the employment of combinations of quickly and slowly degradable polymers in encapsulating drugs. From the quantity of the drug released from the microparticles made of the combined polymers, however, the release rate of the drug from the microparticles cannot be determined accurately. Under the coexistence of at least two different polymers in one microparticle, the more slowly degradable polymer tends to be degraded at a faster rate owing to the degradation products of the faster degradable polymer than under its sole existence. In result, the release rate of drugs in the body is also affected by the faster degradable polymer and thus, different from the average value of the release rates of drugs encapsulated in individual polymers.

To circumvent this problem, the same active ingredients are encapsulated in at least two individual polymers which are different in degradation rate from each other and the microcapsules are combined at appropriate ratios to give a microcapsule dosage formulation which can release the active ingredients for a desired period of time, as disclosed in U.S. Pat. No. 4,897,268. However, this technique is cumbersome in that two or more types of microcapsules are needed for one drug dosage form and thus is unfavorable economically.

SUMMARY OF THE INVENTION

It is an object of the present invention to provide a method for preparing a sustained drug release formulation composed of various microparticles which retain their drug release properties in their integrity, whereby the release period of time of the formulation can be easy to expect and be controlled by varying compositions and molecular weights of polymers, compositions and concentrations of solvents, and kinds and amounts of additives.

It is another object of the present invention to provide a sustained drug release formulation which can release drugs of interest for a desired period of time.

In accordance with the present invention, a sustained drug release formulation can be prepared using a multi-emulsion process, which comprises the steps of: dissolving or dispersing a drug in each of at least two oils to give at least two primary oil phases or emulsions, each containing a biodegradable polymer; dispersing the at least two primary oil phases or emulsions in one aqueous phase, synchronously or in succession; and removing the organic solvents from the drug-dispersed solution to produce microparticles.

In the present invention, LHRH analogues can be encapsulated in an excipient made of a biodegradable aliphatic polyester and continuously released in vivo for a desired period of time.

BRIEF DESCRIPTION OF THE INVENTION

The above and other objects, features and other advantages of the present invention will be more clearly understood from the following detailed description taken in conjunction with the accompanying drawings, in which:

FIG. 1*a* is an optical photograph of microparticles prepared in accordance with Example I.

FIG. 1*b* is an optical photograph of microparticles prepared in accordance with Comparative Example Ia of the present invention.

FIG. 1*c* is an optical photograph of microparticles prepared in accordance with Comparative Example Ib.

FIG. 1*d* is an optical photograph of microparticles prepared in accordance with Comparative Example Ic.

FIG. 2*a* is a scanning electron microphotograph of microparticles prepared in accordance with Example IIA of the present invention, magnified by 100 times.

FIG. 2*b* is a scanning electron microphotograph of microparticles prepared in accordance with Example IIA of the present invention, magnified by 800 times.

DETAILED DESCRIPTION OF THE INVENTION

Figure 1A:
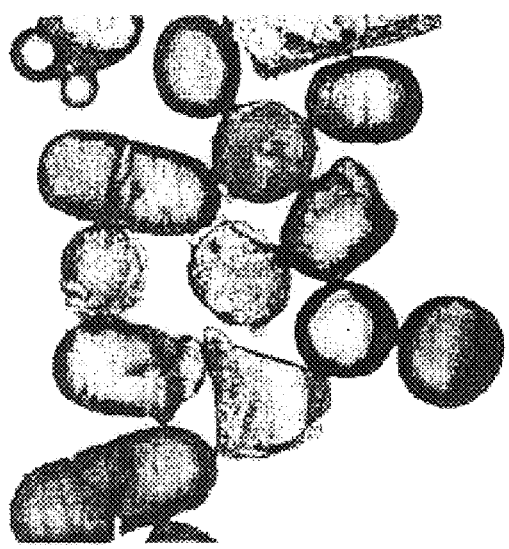

The present invention contemplates the synchronous or successive dispersion of various primary oil phases or emulsions in one aqueous phase to prepare a mixture of microparticles which keep their individual releasing properties intact and thus allow the preparation of a drug delivery system capable of continuously releasing drugs for a prolonged period of time. Over conventional methods, the present invention has an advantage of controlling factors regarding the releasing time period with ease, especially the initial releasing rate without altering the total releasing time period.

In the present invention, there is introduced a process of controlling the compositions and molecular weights of suitable polymers, the compositions and concentrations of solvents and additives in a variety of levels, leading to the sustained release microparticle preparation which is summarized in the following three steps:

First step: At least two primary oil phases (oil) or emulsions (water in oil) are prepared which are different from each other in at least two of the kinds, compositions and concentrations of active ingredients and biodegradable polymers.

Second step: The primary oils or water-in-oils are dispersed in one aqueous phase (water).

Third step: The organic solvent is removed from the dispersion to give microparticles.

In regard to the dispersion of the second step, the two or more primary oil phases or emulsions are, in succession, dispersed in one aqueous phase. Alternatively, one of the primary oil phases or emulsions is first dispersed in an aqueous phase which is allowed to undergo a change in its physical or chemical factors, followed by the dispersion of the other oil phase(s) in the aqueous phase. The term "physical or chemical factors" as used herein means mixer speeds, aqueous phase amounts, and the concentrations of the emulsifiers or additives contained in the aqueous phase.

Concrete, but not limitative, examples of the biodegradable polymers suitable for use in the present invention include cellulose acetate, cellulose acetate propionate, cellulose butyrate, cellulose propionate, cellulose valerate, cumaroneindene polymer, dibutylaminohydroxypropyl ether, ethyl cellulose, ethylene-vinyl acetate copolymer, glycerol distearate, hydroxypropylmethyl cellulose phthalate, 2-methyl-5-vinylpyridine methacrylate-methacrylic acid copolymer, polyamino acids, polyanhydrides, polycaprolactone, polycarbonate, polybutadiene, polyesters, aliphatic polyesters, polybutadiene, polyesters, polyhydroxybutyric acid, polymethyl methacrylate, polymethacrylic acid ester, polyolesters, polypropylene, polysaccharides such as alginic acid, chitin, chitosan, chondroitin, dextrin, dextran, hyaluronic acid, heparin, keratan sulfate, starch and so forth, polystyrene, polyvinyl acetal diethylamino acetate, polyvinyl acetate, polyvinyl alcohol, polyvinyl butyral, polyvinyl formal, proteins such as albumin, casein, collagen, fibrin, fibrinogen, gelatin, hemoglobin, transfferin, zein and so forth, vinylchloride-propylene-vinlyacetate copolymer, vinylchloride-vinylacetate polymer, waxes such as beef tallow, whale wax, bee wax, paraffin wax, castor wax and so forth, and higher lipid acids such as myristic acid, palmitic acid, stearic acid, behenic acid and so forth with preference to aliphatic polyesters. More preferable are polylactides, polyglycolides and copolymers thereof (PLGA).

A more detailed description will be given of the present invention by taking an instance of PLGA.

Degraded finally into lactic acid and glycolic acid in vivo, PLGA is acknowledged to be biocompatible and harmless to the body. With this advantage, PLGA, which acquired the permission of the FDA, U.S.A. for its use in the body, is applied for the sustained drug delivery systems for leutenizing hormone release hormone (LHRH) analogues which are used in the treatment of prostatic cancer and for human growth hormone which is administered to patients suffering from infantile nanism. Existing in various forms in dependence on its physical properties such as proportions between the constituent monomers lactic acid and glycolic acid, molecular weight, and hydrophilicity, PLGA is degraded in vivo for a period of two weeks to several months.

In the first step of the method according to the present invention, at least two primary oil phases or emulsions are prepared. These oil phases or emulsions are different in physical and chemical properties of PLGA. For instance, one of the primary oil phases or emulsions may be made by dissolving in an oil a drug and a PLGA which is degraded within a relatively short period of time in vivo. Such a fast degradable PLGA can be prepared from a mixture of, for example, 50:50 lactic acid:glycolic acid. Highly hydrophilic PLGA, for example, PLGA containing terminal carboxyl residues such as RG502H and RG503H (Boehringer Ingelheim), and low molecular weight PLGA show high degradation rates. On the other hand, for the preparation of another or the other primary phase or emulsion, the same drug and a relatively slowly degradable PLGA may be employed. As for the relatively slowly degradable PLGA, it can be prepared from a mixture of, for example, 75:25 lactic acid:glycolic acid. PLGA of low hydrophilicity, for example, PLGA whose terminal carboxyl groups are substituted by dedecyl, such as RG502 and RG503 (Boehringer Ingelheim), and high molecular weight PLGA show low degradation rates. When a water-soluble drug is used, it is dissolved in an aqueous phase and then emulsified in the oil phases which contain respective polymers, thereby producing at least two primary emulsions.

Also, the oil phases or emulsions may be different in the drugs they retain while the same polymer may be employed. In detail, where LHRH is used as an active ingredient, two different primary oil phases may be obtained by dissolving an antagonistic LHRH in one oil phase and an agonistic LHRH analogue in another primary oil.

In addition, at least two physically or chemically different primary oil phases or emulsions can be prepared using not different kinds of drugs or polymers, but one drug and one polymer. In this case, the parameters determining the difference in physical and/or chemical properties between two or more primary oil phases or emulsions include the weight ratio of drug to polymer, the weight ratio of drug or polymer to organic solvent, the weight ratio between organic solvents (if two or more organic solvents are used), and the weight ratio of an organic solvent to an aqueous solvent (if the drug is water soluble, that is, when W/O/W is used). The microparticles prepared with different parameters are different from one to another in structure and morphology as well as in drug release rate. For instance, if the weight ratio of the polymer to the organic solvent is increased, the primary oil phase or emulsion has an increased viscosity and thus, shows an improved encapsulation efficiency, resulting in the production of enlarged microparticles. As another example, in the case that the drug is water soluble, the release rate tends to increase as the content rate of the drug increases. On the other hand, the release rate of lipid-soluble drug has a tendency toward decreasing when the content rate of the drug increases.

Different chemical and physical properties can also result from the use of a mixture of different solvents. Since different solvents show dissimilarity in water solubility as well as in boiling point from each other, the solvents are removed or evaporated at different rates from the emulsion dispersed in the secondary aqueous phase. In result, the microparticles show different properties enough to affect their drug release rates.

In the second step of the method according to the present invention, the two or more primary oil phases or emulsions prepared above are dispersed in one aqueous phase. The dispersion of the primary oil phases or emulsions may be conducted synchronously or in succession. In the latter case, the secondary oil phase may be dispersed shortly after the dispersing of the first primary oil phase or emulsion in an aqueous phase. These dispersing techniques must use such a sufficient quantity of the aqueous phase as to extract or evaporate the organic solvent present in the primary oil phase or emulsion. In addition, the successive dispersing of the primary oil phases or emulsions may be achieved by introducing the step of changing the physical and chemical factors of the aqueous phase between the dispersing steps of the first primary oil phase or emulsion and the second primary oil phase or emulsion.

As mentioned above, the physical and chemical factors of the aqueous phase include mixer speeds, aqueous phase amounts, and the concentrations of the emulsifiers or additives contained in the aqueous phase. On the whole, increasing the mixing speed reduces the size of the emulsified micelles, resulting in a decrease in the size of microparticles. A large quantity of the aqueous phase allows the organic solvents to be extracted at a high rate from the emulsion, bringing about a high speed in the solidification of the biodegradable polymer. In result, large size microparticles are formed. The temperature of the aqueous phase also must be taken into account because it has an influence on the evaporation rate of the organic solvents. As the temperature is raised, the evaporation becomes fast. As a result, the solidification rate of the biodegradable polymer and the size of the microparticles determine the drug release rate. After the dispersing of the first primary oil phase or emulsion in an aqueous phase, increasing the amount or temperature of the aqueous phase leads to the extraction of a sufficient amount of the organic solvent contained in the second primary oil phase or emulsion. In dispersing at least two primary oil phases or emulsions in one aqueous phase, therefore, account must be taken of the kind and amount of the organic solvent present in each of the primary oil phases or emulsions as well as of the amount and temperature of the aqueous phase.

By way of examples, but not limitation, drugs suitable for use in the present invention include physiologically active peptides and/or proteins, anti-cancer agents, antibiotics, antifebriles, acesodynes, anti-inflammatory agents, expectorants, abirritants, muscle relaxants, epilepsy remedies, anti-ulcerative agents, anti-hypochondriac agents, anti-allergic agents, cardiants, anti-arrhythmic agents, vasodilatative agents, hypotensive hydragogues, diabetes curatives, hyperlipemie remedies, anticoagulants, hemolytic agents, antituberculous agents, hormones, anesthetic antagonists, osteoclastic suppressants, osteogenic promotives, angiogenesis suppressors, and mixtures thereof.

Composed of at least two amino acids, the physiologically active peptides and/or proteins range, in molecular weight, from 200 to 100,000 and can be exemplified by human growth hormone, growth hormone releasing hormone, growth hormone releasing peptide, interferon, colony stimulating factors, interleukin, macrophage activating factors, macrophage peptide, B-cell factors, T-cell factors, protein A, allergy repressors, cell necrosis glycoproteins, immunotoxins, lymphotoxins, tumor necrosis factors, tumor repression factors, metastasis growth factors, $\alpha$-1 antitrypsin, albumin and its polypeptide fragments, apolipoprotein-E, erythropoietin, Factor VII, Factor VIII, Factor IX, plasminogen activating factors, urokinase, streptokinase, Protein C, C-reactive proteins, renin suppressants, collagenase suppressants, superoxide dismutase, platelet-derived growth factors, epidermal growth factors, osteogenic growth factors, osteogenic promoting proteins, calcitonin, insulin, atriopeptin, cartilage induction factors, connective tissue activating factors, follicle stimulating hormone, leutenizing hormone, leutenizing hormone releasing hormone, nerve growth factors, parathyroid hormone, relaxin, secretin, somatomedin, insulin-like growth factors, adrenocoticotrophic hormone, glucagons, cholecystokinin, pancreatic polypeptides, gastrin releasing hormone, coticotrophin releasing factors, thyroid stimulating hormones, mono- and poly-clonal antibodies against various viruses, bacteria and toxins, various virus-derived vaccines, and mixtures thereof.

Non-limitative, concrete examples of the anticancer agents include bleomycin, methotrexate, actinomycin D, mitomycin C, binblastin sulfate, bincrystin sulfate, daunorubicin, adriamycin, neocartinostatin, cytosinearabinoside, fluorouracil, tetrahydrofuryl-5-fluorouracil, krestin, picibanil, lentinan, levamisole, bestatin, azimexon, glycyrrhizin, polyls such as polyl:C, polylA:U, and polylCLC.

Concrete examples of the antibiotics useful in the present invention include gentamicin, dibekacin, kanendomycin, lividomycin, tobramycin, amikacin, fradiomycin, sisomycin, tetracycline hydrochloride, oxytetracucline hydrochloride, rolitetracycline, doxycycline hydrochloride, ampicillin, peperacillin, ticarcillin, ceflothin, cefaloridine, cefotiam, cefsulodin, cefmenoxime, cefmetazole, cefazolin, cefotaxime, cefoperazon, ceftizoxime, mochisalctam, thienamycin, sulfazecin and asetreonam.

Antifebriles applicable for the present invention are exemplified by analgesics, salicylic acid-containing anti-inflammatory agents, sulpyrine, flufenamic acid, diclofenac, indomethacin, morphine, pethidine hydrochloride, levorphanol tartarate and oxymorphone, but are not limited thereto.

Non-limiting, concrete examples of the acesodynes usable in the present invention include ephedrine hydrochloride, methylphedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproterenol hydrochloride, sulbutamol sulfate and terbutaline sulfate.

As for the abirritants, they are exemplified by chlorpromazine, prochlorperazine, trifltioperazine, atropine sulfate, and methyiscopolamine bromide.

As examples of the muscle relaxants, there are pridinol methanesulfonate, tubocurarine chloride, and pancuronium bromide.

As examples of the epilepsy remedies, there are phenytonin-containing antiepileptics, ethosuximide, acetazolamide sodium chlordiazepoxide.

Examples of the anti-ulcerative agents include metoclopramide and histidine hydrochloride.

Examples of the anti-hypochondriac agents include imipramine, clomipramine, noxiptiline and phenerdine sulfate.

Examples of the anti-allergic agents include diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride.

As examples of the cardiants, there are transpaioxocamphor, theophyllol, aminophylline, and etilefrine hydrochloride.

The anti-arrhythmic agents may be exemplified by propranol, alprenolol, bufetolol and oxprenolol.

Examples of the vasodilatative agents useful in the present invention include oxyfedrine hydrochloride, diltiazem, tolazoline hydrochloride, hexobendine, and bamethan sulfate.

Examples of the hypotensive hydragogues include hexamethonium bromide, pentolinium, mecamylamine hydrochloride, ecarazine hydrochloride and clonidine.

As examples of the diabetes curatives, there are glymidine sodium, glipizide, fenformin hydrochloride, buformin hydrochloride and metformin.

As examples of the hyperlipemie remedies, there are pravastatin sodium, simvastatin, clinofibrate, clofibrate, simfibrate and bezafibrate.

Useful as the anticoagulant is heparin sodium.

Examples of the hemolytic agents include thromboplastin, thrombin, menadione sodium hydrogen sulfite, acetomenaphthone, tranexamnic acid, carbozochrome sodium fulfonate and adrenochrome monoaminoguanidine methanesulfonate.

Examples of the antituberculous agents include isoniazid, ethambutol and p-aminosalicylic acid.

Available as hormones in the present invention are predonisolone, predonisolone sodium phosphate, dexamethasone sodium sulfate, betamethasone sodium phosphate, hexestrol phosphate, hexestrol acetate and methimazole.

The anesthetic antagonists may be exemplified by levallorphan tartrate, nalorphine hydrochloride and naloxone hydrochoride.

As an osteoclastic suppressant ipriflavone can be applied for the present invention. As the osteogenic promotives available in the present invention, peptides peptides such as BMP, PTH, TGF-beta and IGF-1.

Examples of the angiogenesis suppressors include steroids, fumagillin and fumagillol.

The above physiologically active drugs may be in pharmaceutically applicable salt forms. For instance, for the physiologically active drugs which contain basic radicals such as amine groups, inorganic acids such as hydrochloric acid, sulfuric acid and nitric acid and organic acids such as carbonic acid and succinic acid are usefully used. Where the physiologically active drugs contain acidic radicals such as carboxylic acids, inorganic salts such as sodium and potassium and basic organic compounds such as triethyl amine and arginine are useful to change the drugs of interest into pharmaceutically acceptable salts.

A better understanding of the present invention may be obtained in light of the following examples which are set forth to illustrate, but are not to be construed to limit the present invention.

EXAMPLE I

Preparation of Mixture of Brilliant Blue-Encapsulating Microparticles and Rhodamin-Containing Microparticles (1:1) by Double Emulsification 0.1 g of Brilliant Blue was dissolved in 1.5 g of methanol and dispersed in a solution of 0.5 g of RG502H (Boehringer Ingelheim) in 2.0 g of methylene chloride to give a primary emulsion DP1. Separately, a solution of 0.1 g of rhodamin in 1.5 g of methanol was dispersed in 2.0 g of methylene chloride containing 0.5 g of RG502H to give a primary emulsion DP2. The primary emulsions DP1 and DP2 were, in succession, dispersed in 250 ml of a 0.5% polyvinyl alcohol solution in water preheated at 25° C. while being stirred at 3,500 rpm by use of a homogenizer. After the stirring was conducted at 3,000 rpm for an additional 15 min to give an emulsion, the organic solvent was evaporated at 40° C. for one hour to produce solidified microparticles. They are shown in the optical microphotograph of FIG. 1a.

COMPARATIVE EXAMPLE I

Figure 1B:
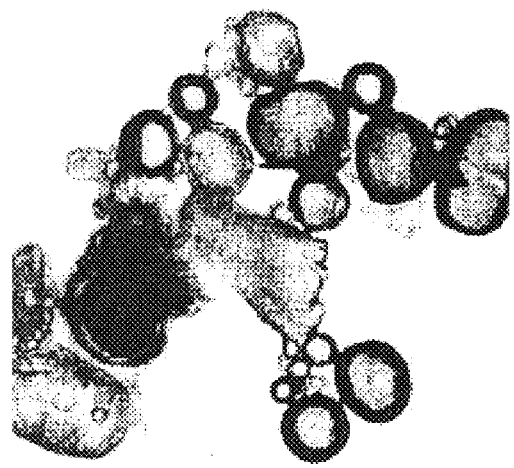

A: Preparation of Brilliant Blue-Encapsulating Microparticles 0.1 g of Brilliant Blue was dissolved in 1.5 g of methanol and dispersed in a solution of 1 g of RG502H (Boehringer Ingelheim) in 2.0 g of methylene chloride to give a primary emulsion. The primary emulsion was dispersed in 250 ml of a 0.5% polyvinyl alcohol solution in water preheated at 25° C. while being stirred at 3,500 rpm by use of a homogenizer. After the stirring was conducted at 3,000 rpm for an additional 15 min to give an emulsion, the organic solvent was evaporated at 40° C. for one hour to produce solidified microparticles. FIG. 1b is an optical microphotograph of the microparticles.

Figure 1C:
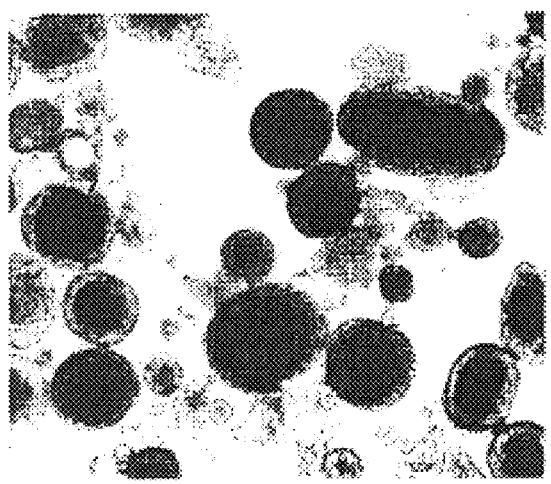
Figure 1D:

B: Preparation of Rhodamin-Encapsulating Microparticles 0.2 g of Rhodamin was dissolved in 3 g of methanol and dispersed in a solution of 1 g of RG502H (Boehringer Ingelheim) in 2.0 g of methylene chloride to give a primary emulsion. The primary emulsion was dispersed in 250 ml of a 0.5% polyvinyl alcohol solution in water preheated at 25° C. while being stirred at 3,500 rpm by use of a homogenizer. After the stirring teas conducted at 3,000 rpm for an additional 15 min to give an emulsion, the organic solvent was evaporated at 40° C. for one hour to produce solidified microparticles. FIG. 1c is an optical microphotograph of the microparticles.

C: Preparation of Brilliant Blue/Rhodamin (1:1)-Encapsulating Microparticles by Polymer Mixing Method Along with 0.1 g of Brilliant Blue, 0.1 g of Rhodamin was dissolved in 3 g of methanol, followed by dispersing the methanol solution in a polymeric solution of 1 g of RG502H in 2.0 g of methylene chloride to give a primary emulsion. The primary emulsion was dispersed in 250 ml of a 0.5% polyvinyl alcohol solution in water preheated at 25° C. while being stirred at 3,500 rpm by use of a homogenizer. After the stirring was conducted at 3,000 rpm for an additional 15 min to give an emulsion, the organic solvent was evaporated at 40° C. for one hour to produce solidified microparticles. FIG. 1c is an optical microphotograph of the microparticles.

As shown in the respective optical microphotographs of FIGS. 1a to 1d for Example I and Comparative Examples 1A to 1C, the microparticles prepared in Example I are in the mixture of equal quantities of those prepared in Comparative Examples IA and IB while the microparticles prepared by the polymer mixing method of Comparative Example IC took a mixed color of the two.

EXAMPLE II

Preparation of Leuprolide Acetate-Encapsulating Biodegradable Microparticle with Continuous Drug Release Capacity for 28 Days or Longer A-Type: In 0.28 g of methanol was dissolved 62.5 mg of leuprolide acetate. This methanol solution was dispersed in 1.125 g of methylene chloride containing 0.438 g of a PLGA (RG502H, Boehringer Ingelheim) which has a molecular weight of 8,600 with 50:50 lactide:glycolide to give a primary emulsion DP1. Separately, 62.5 mg of leuprolide acetate was dissolved in 0.37 g of methanol, followed by dispersing the methanol solution in 1.313 g of methylene chloride containing 0.438 g of a PLGA (RG503H, Boehringer Ingelheim) which has a molecular weight of 33,000 with 50:50 lactide:glycolide, to give a primary emulsion DP2. The primary emulsions DP1 and DP2 were, in succession, dispersed in 250 ml of a 0.3% polyvinyl alcohol solution in water preheated at 25° C. while being stirred at 3,500 rpm by use of a homogenizer. After the stirring was conducted at 3,000 rpm for an additional 15 min to give an emulsion, the organic solvent was evaporated at 40° C. for two hours to produce solidified microparticles.

Figure 2A:
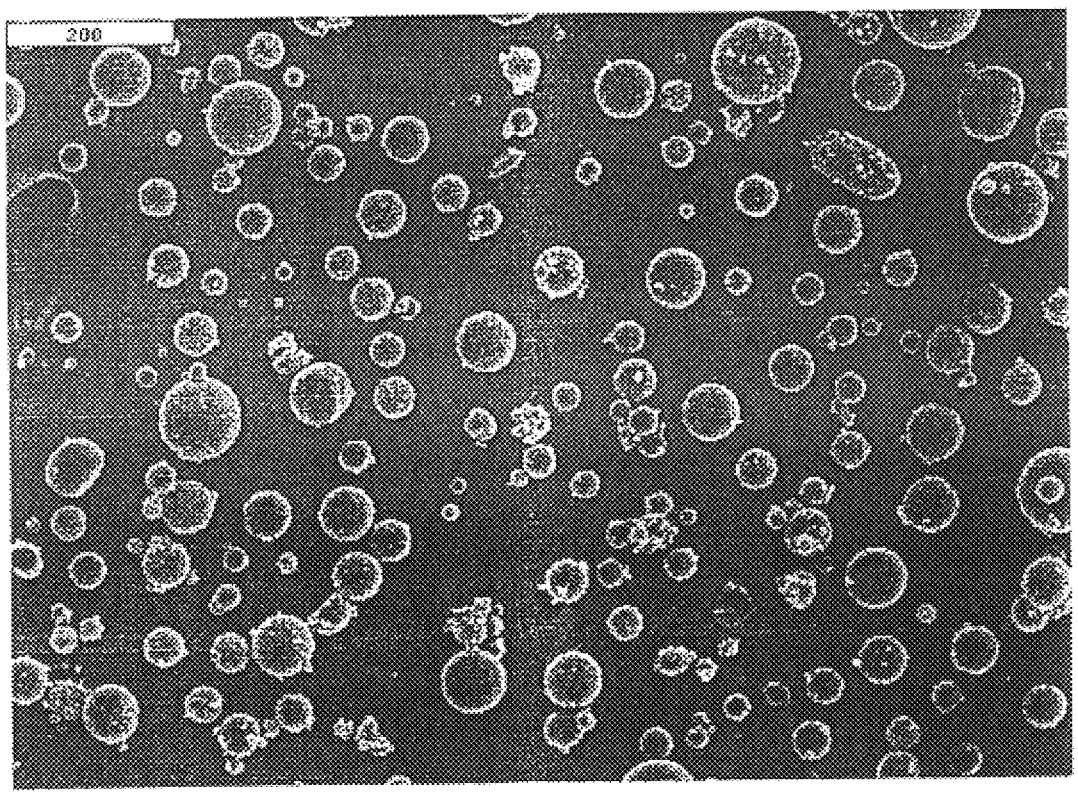
Figure 2B:
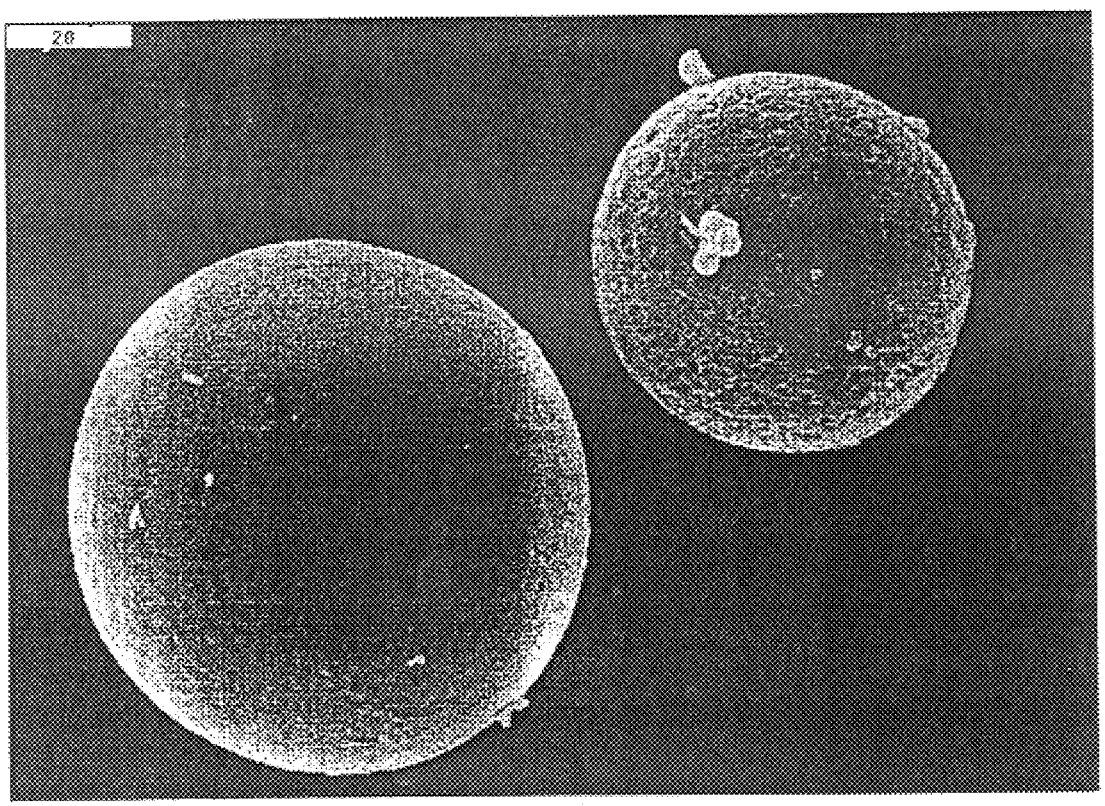

The microparticles are shown in scanning electron microphotographs of FIG. 2, magnified by 100 times (a) and 800 times (b). In the SEM of FIG. 2b, the right microparticle is observed to have pores derived from the 502H polymer of the emulsion DP1 while the left microparticle is seen as being non-porous, derived from the 503H of the emulsion DP2.

B-Type: 75 mg of leuprolide acetate was dissolved in 0.27 g of methanol and dispersed in 1.093 g of methylene chloride containing 0.425 g of RG502H to give a primary emulsion DP1. Separately, a solution of 75 mg of leuprolide acetate in 0.36 g of methanol was dispersed in a polymeric solution of 0.425 g of RG503H in 1.275 g of methylene chloride to give a primary emulsion DP2. Thereafter, microparticles were prepared by following the remaining procedure for the A-type of Example 2.

COMPARATIVE EXAMPLE II

A: Preparation of Leuprolide Acetate-Encapsulating RG502H Microparticle 62.5 mg of leuprolide acetate was dissolved in 0.28 g of methanol and dispersed in 1.125 g of methylene chloride containing 0.438 g of RG502H to give a primary emulsion. The primary emulsion was dispersed in 125 ml of a 0.3% polyvinyl alcohol solution in water preheated at 25° C. while being stirred at 3,500 rpm by use of a homogenizer. Thereafter, microparticles were prepared by following the remaining procedure for the A-type of Example 2.

B: Preparation of Leuprolide Acetate-Encapsulating RG503H Microparticle 62.5 mg of leupiolide acetate was dissolved in 0.378 g of methanol and dispersed in 1.313 g of methylene chloride containing 0.438 g of RG503H to give a primary emulsion. The primary emulsion was dispersed in 125 ml of a 0.3% polyvinyl alcohol solution in distilled water preheated at 25° C. while being stirred at 3,500 rpm by use of a homogenizer. Thereafter, microparticles were prepared by following the remaining procedure for the A-type of Example 2.

C: Preparation of Leuprolide Acetate-Encapsulating RGS502G/RG503H (1:1) Microparticle In 0.65 g of methanol was dissolved 125 mg of leuprolide acetate which was then dispersed in a solution of 0.438 g of RG502H and 0.438 g of RG503H in 2.438 g of methylene chloride to obtain a primary emulsion. This emulsion was dispersed in 250 ml of a 0.3% polyvinyl alcohol solution in distilled water preheated at 25° C. while being stirred at 3,500 rpm by use of a homogenizer. Thereafter, microparticles were prepared by following the remaining procedure for the A-type of Example 2.

TEST EXAMPLE I

In vitro Drug Release of Microparticles

Figure 3:
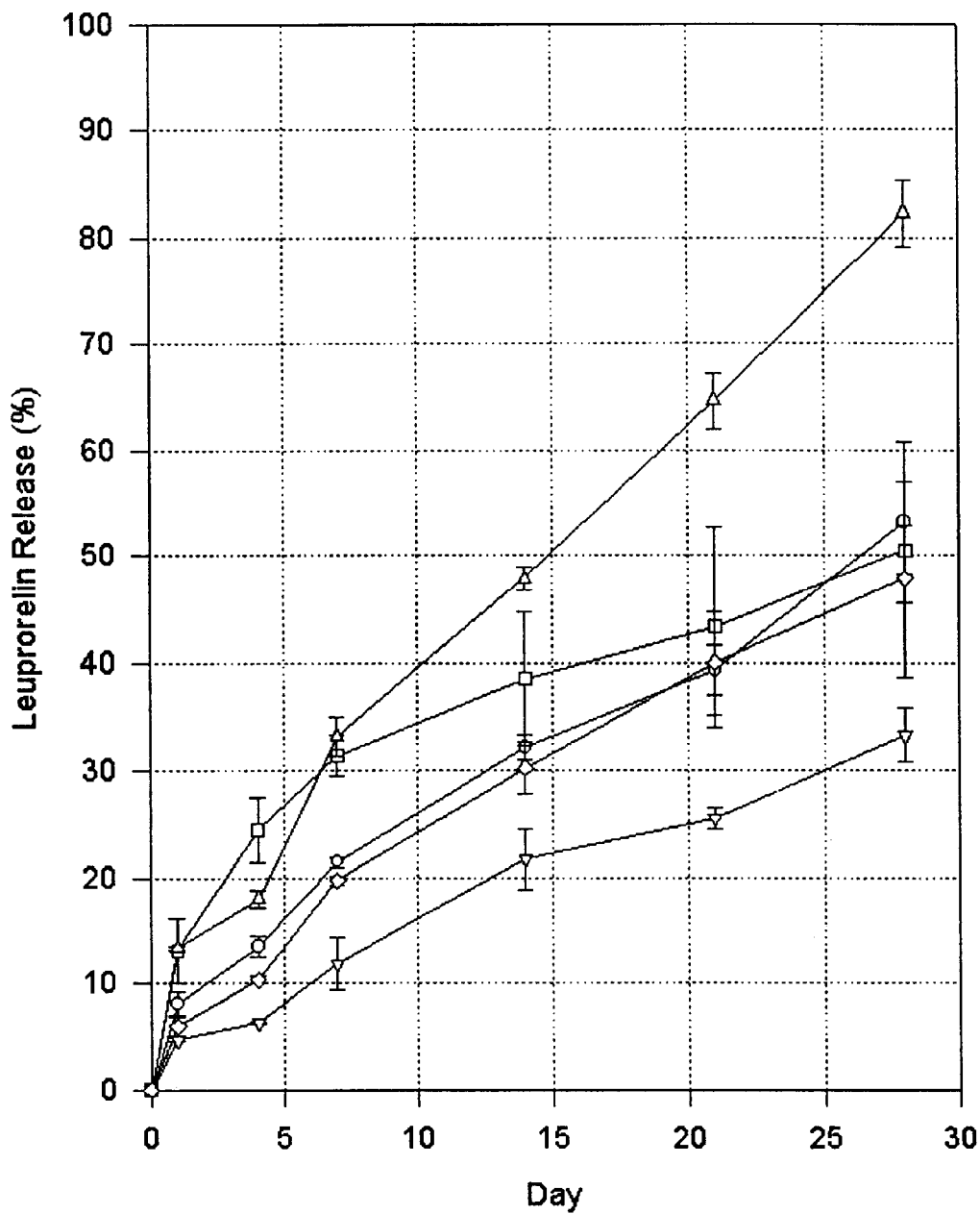
FIG. 3 is a graph showing in vitro release test results of various microparticles, including Leuplin (-□-) and microparticles prepared in Comparative Example IIA (-△-), Comparative Example IIB (-▽-), Example IIA (-○-), and Example IIB (-◇-).

The biodegradable microparticles prepared in Example II and Comparative Example II were tested, along with commercially available Leuplin (Takeda, Japan) as a control, for in vitro drug release as follows. 5 mg of each of the freeze-dried microparticles was dispersed in 35 vials, each containing a 0.033M phosphate buffer (pH 7), and allowed to release the drug at 37° C. On the day of the testing and the 1st day, the 4th day, the 7th day, the 14th day, the 21st day and the 28th day after the testing, each of the test samples was taken from five vials and centrifuged. The microparticles thus obtained were extracted with a methylene chloride/acetate (1:1 v/v) buffer and the leuprolide transferred into the acetate layer was quantified by HPLC at 280 nm with a mobile phase of an aqueous 28% acetonitrile solution containing 0.1% trifluoroacetic acid at a flow rate of 1.0 ml/min. The results were shown in FIG. 3.

TEST EXAMPLE II

Level of Leuprolelin in Blood

Figure 4:
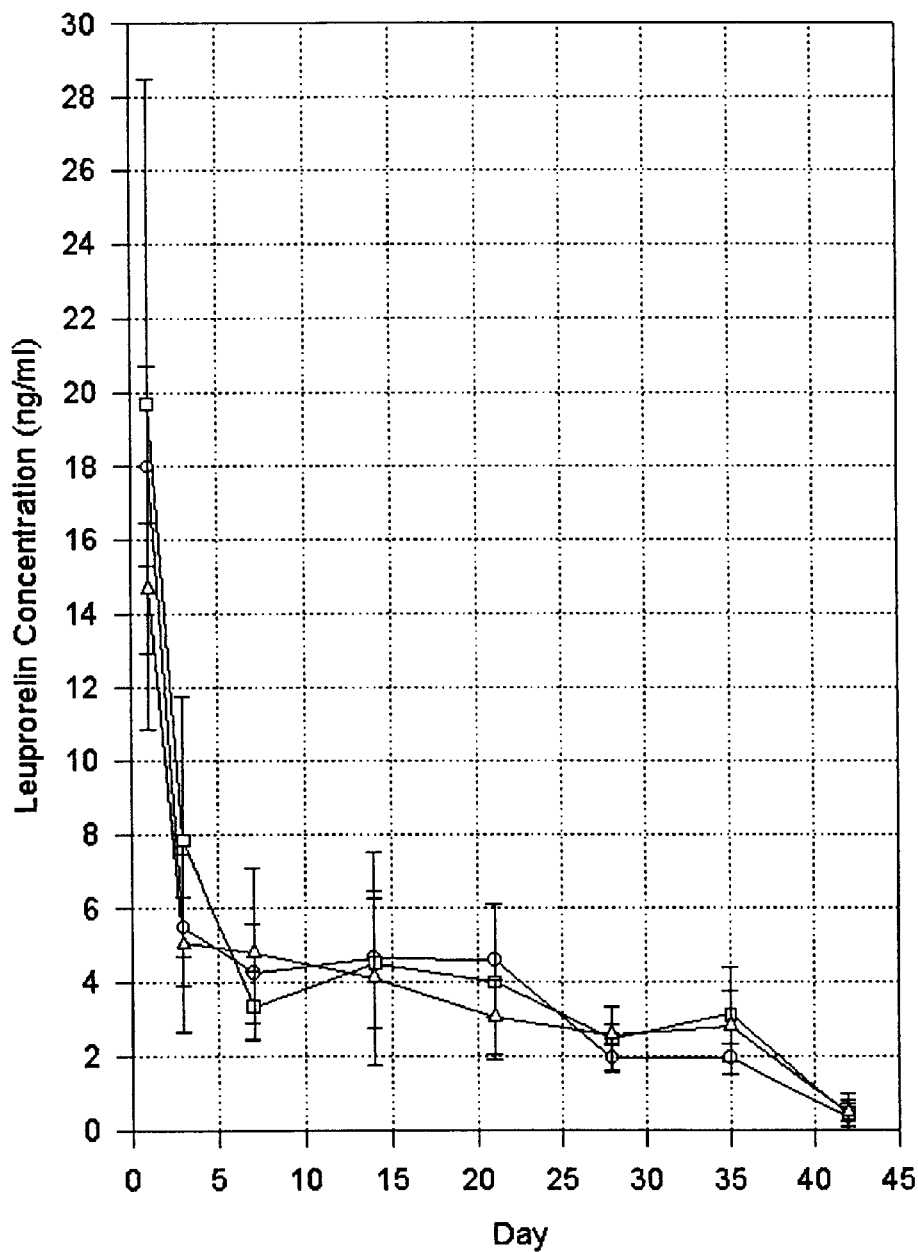
FIG. 4 is a graph showing in vivo release test results of various microparticles, including Leuplin (-□-) and microparticles prepared in Example IIA (-○-) and Example IIB (-△-)
Figure 5:
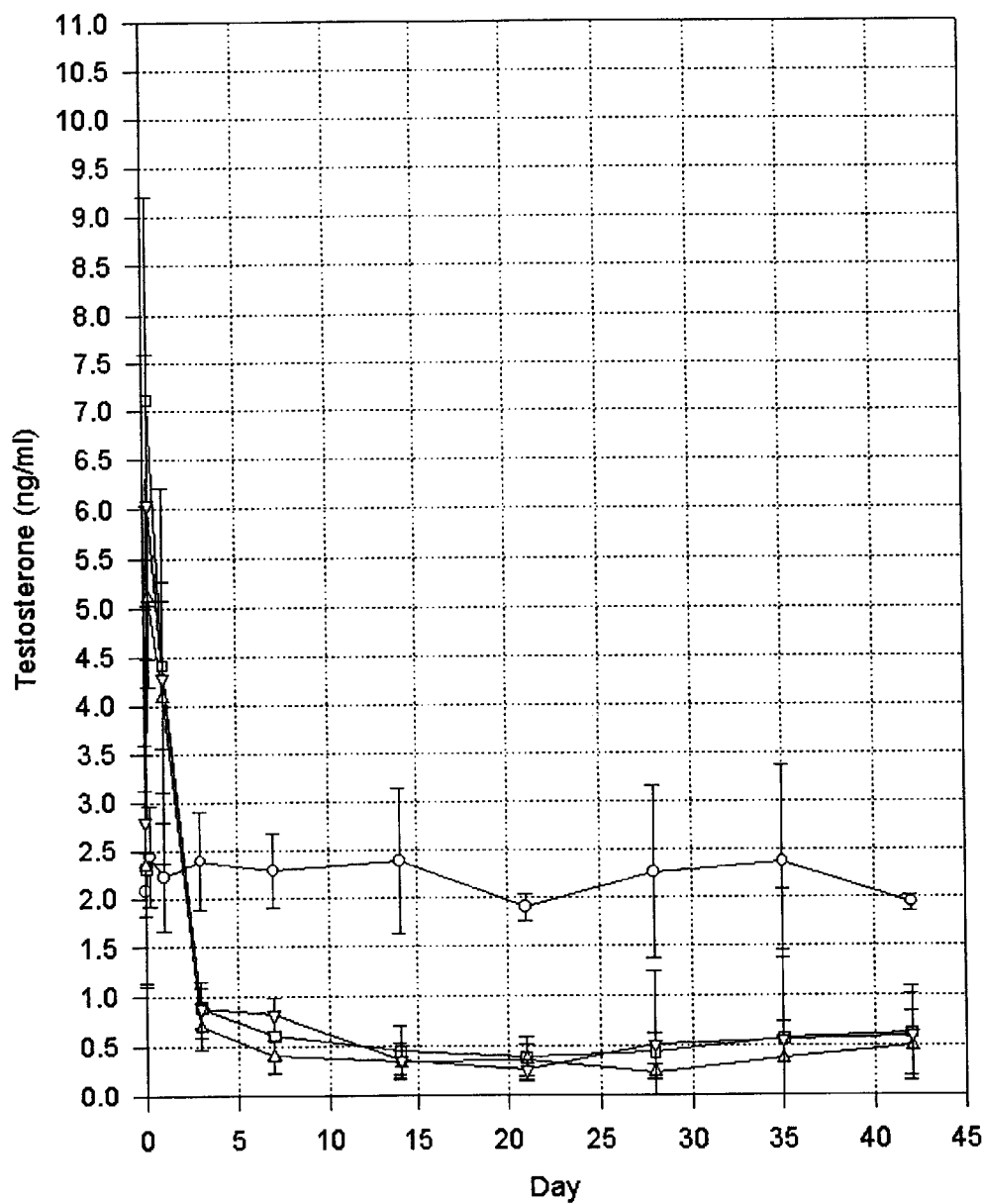
FIG. 5 is a graph showing in vivo testosterone repressing effects of a control (-○-), Leuplin (-□-) and microparticles prepared in Example IIA (-△-) and Example IIB (-▽-).

The biodegradable microparticles prepared in Example II were tested, along with commercially available Leuplin (Takeda, Japan) as a control, for in vivo drug release as follows. For the determination of the drug release capacity, the leuprolelin levels in blood were quantified. 10 male SD rats were used for this test. The microparticles prepared in Example II were introduced into five of the male SD rats via intramuscular injection while Leuplin was intramuscularly injected into the other five rats. The microparticles were administered at a dose of 0.9 mg per rat. Blood samples were taken from a tail vein of each of the rats on one day, three days, seven days, 14 days, 21 days, 28 days and 35 days after the injection and measured for leuprolelin level. The results are shown in FIG. 4.

TEST EXAMPLE III

Level of Testosterone in Blood

The biodegradable microparticles prepared in Example II were tested, along with commercially available Leuplin (Takeda, Japan) as a control, for in vivo drug activity as follows. For the determination of the drug activity, the testosterone levels in blood were quantified. 10 male SD rats were used for this test. The microparticles prepared in Example II were introduced into five of the male SD rats via intramuscular injection while Leuplin was intramuscularly injected into the other five rats. The microparticles were administered at a dose of 0.9 mg per rat. Blood samples were taken from a tail vein of each of the rats on one day, three days, seven days, 14 days, 21 days, 28 days and 35 days after the injection and measured for leuprolelin level. The results are shown in FIG. 4.

EXAMPLE III

Preparation of Adriamycin-Encapsulating Biodegradable Microparticle with Continuous Drug Release Capacity of Two Months or Longer In 0.563 g of methanol was dissolved 20 mg of adriamycin. This methanol solution was dispersed in 2.253 g of methylene chloride containing 0.875 g of RG502H to give a primary emulsion DP1. Separately, 15 mg of adriamycin was dissolved in 0.735 g of methanol, followed by dispersing the methanol solution in 2.624 g of methylene chloride containing 0.875 g of a PLGA (RG502, Boehringer Ingelheim) which has a molecular weight of 14,500 with 50:50 lactide:glycolide, to give a primary emulsion DP2.

The primary emulsions DP1 and DP2 were synchronously dispersed in 500 ml of a 0.3% polyvinyl alcohol solution in water preheated at 25° C. while being stirred at 3,500 rpm by use of a homogenizer. Thereafter, microparticles were prepared by following the remaining procedure for the A-type of Example 2.

EXAMPLE IV

Preparation of Leuprolide Acetate-Encapsulating Biodegradable Microparticle with Continuous Drug Release Capacity of Three Months or Longer A-Type: In 0.282 g of methanol was dissolved 62.5 mg of leuprolide acetate. This methanol solution was dispersed in 1.127 g of methylene chloride containing 0.438 g of RG502H to give a primary emulsion DP1. Separately, 187.5 mg of leuprolide acetate was dissolved in 0.492 g of methanol, followed by dispersing the methanol solution in 1.97 g of methylene chloride containing 1.3 g of polylactide (PLA0015, Wako, Japan) which has a molecular weight of 15,000, to give a primary emulsion DP2. The primary emulsions DP1 and DP2 were, in succession, dispersed in 500 ml of a 0.3% polyvinyl alcohol solution in water preheated at 25° C. while being stirred at 3,500 rpm by use of a homogenizer. Thereafter, microparticles were prepared by following the remaining procedure for the A-type of Example 2.

B-Type: 125 mg of leuprolide acetate was dissolved in 0.328 g of methanol and dispersed in 1.3 g of methylene chloride containing 0.875 g of PLA0015 to give a primary emulsion. Half of the primary emulsion was dispersed in 125 ml of a 0.1% polyvinyl alcohol solution in distilled water while being stirred at 3,500 rpm with the aid of a homogenizer. In this dispersion, 125 ml of a 0.3% polyvinyl alcohol solution of distilled water was slowly added, after which the temperature was controlled to 25° C. and the other half of the primary emulsion was dispersed. Thereafter, microparticles were prepared by following the remaining procedure for the A-type of Example 2.

EXAMPLE V

Preparation of Leuprolide Acetate-Encapsulating Biodegradable Microparticle with Continuous Drug Release Capacity of Four Months or Longer In 0.282 g of methanol was dissolved 62.5 mg of leuprolide acetate. This methanol solution was dispersed in 1.127 g of methylene chloride containing 0.438 g of RG502H to give a primary emulsion DP1. Separately, 187.5 mg of leuprolide acetate was dissolved in 0.492 g of methanol, followed by dispersing the methanol solution in 1.97 g of methylene chloride containing 1.3 g of a PLGA (RG502, Boehringer Ingelheim) which has a molecular weight of 14,500 with 50:50 lactide:glycolide, to give a primary emulsion DP2. The primary emulsions DP1 and DP2 were, in succession, dispersed in 500 ml of a 0.3% polyvinyl alcohol solution in water preheated at 25° C. while being stirred at 3,500 rpm by use of a homogenizer. Thereafter, microparticles were prepared by following the remaining procedure for the A-type of Example 2.

EXAMPLE VI

Preparation of Leuprolide Acetate-Encapsulating Biodegradable Microparticle with Continuous Drug Release Capacity of Six Months or Longer In 0.328 g of methanol was dissolved 125 mg of leuprolide acetate. This methanol solution was dispersed in 1.313 g of methylene chloride containing 0.875 g of PLA0015 to give a primary emulsion DP1. Separately, 125 mg of leuprolide acetate was dissolved in 0.735 g of methanol, followed by dispersing the methanol solution in 2.624 g of methylene chloride containing 0.875 g of a PLGA (RG858, Boehringer Ingelheim) which has a molecular weight of 220,000 with 85:15 lactide:glycolide, to give a primary emulsion DP2. The primary emulsions DP1 and DP2 were, in succession, dispersed in 500 ml of a 0.3% polyvinyl alcohol solution in water preheated at 25° C. while being stirred at 3,500 rpm by use of a homogenizer. Thereafter, microparticles were prepared by following the remaining procedure for the A-type of Example 2.

EXAMPLE VII

Preparation of Biodegradable Microparticles Encapsulating Different Polymers

Primary emulsions were obtained using biodegradable polymers as indicated in Table, below, and used to prepare microparticles in similar manners to that of the A-type of Example II.

| | Polymers (Wt. Avg. Mw) | |
|---|---|---|
| Lot No. | DP1 | DP2 |
| DKLP134 | Polybutadiene(8000) | Polylactide(10000) |
| DKLP141 | Polyhydroxybutyrene(9000) | Polyvinylacetate(12000) |
| DKLP146 | Polypropylene(6000) | Polybutadiene(15000) |
| DKLP153 | polyvinylacetate(9000) | Polypropylene(18000) |
| DKLP155 | Polycaprolactone(8500) | Polybutadiene(13000) |
| DKLP162 | Polyvinylbutylal(7000) | Polystyrene(9000) |
| DKLP167 | Polystyrene(6000) | Polyhydroxybutyrene(11000) |

In the above examples, combinations of two primary emulsions which were different in physical and chemical properties from each other were combined in predetermined ratios to prepare microparticles which could continuously release drugs for desired periods of time.

In Table, below, there are summarized theoretical combinations of two emulsions, which are capable of continuously releasing drugs for prolonged periods of time according to polymers (molecular weight, hydrophilicity, polymer/organic solvent, and lactide/glycolide), drugs, and additives.

| Physical and Chemical Factors | | Emulsions | | |
| --- | --- | --- | --- | --- |
| | Affecting | Emulsion 1 | Emulsion 2 | Combination |
| Polymer | Release Properties | Fast Release Rate | Long Release Period Low Initial Release | |
| | Molecular Weight | Small | Large | Continuously |
| | Hydrophilicity | Large | Small | released for |
| | Polymer/Organic Solvent | Small | Large | prolonged |
| | Lactide/Glycolide[1] | Small | Large | periods of time |
| Drug Additives[2] | Drug/Polymer | Large | Small | |
| | Content | Large | Small (or None) | |

[1] Poly(lactide-co-glycolide)
[2] Salts such as $Na^+$ and $Ca^{2+}$, acids such as citric acid and tartaric acid, and amino acids The primary emulsions can be combined in various numbers of cases. For example, four emulsions, which have a large molecular weight, a small molecular weight, an unbalanced ratio between a polymer, and an additive, respectively, may be, in combinations, dispersed synchronously or successively to produce organic solvent microparticles with suitable release periods of time.

As described hereinbefore, microparticle combinations in which the constituent microparticles retain their drug release properties in their integrity can be prepared in a simple process in accordance with the present invention. Therefore, an appropriate combination of the microparticles can release drugs effectively for a desired period of time.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing sustained release microparticles using a multi-emulsion process, comprising
   (a) dissolving or dispersing a drug in each of at least two oils with an organic solvent to give at least a first primary oil phase or emulsion and at least a second primary oil phase or emulsion, each containing a biodegradable polymer;
   (b) dispersing said first primary oil phase or emulsion and said second primary oil phase or emulsion, simultaneously or in succession, in a single aqueous phase to give an o/w emulsion; and
   (c) removing said organic solvent from said o/w emulsion to produce microparticles comprised of said drug and said biodegradable polymer.

2. The method of claim 1, wherein said dispersing in said (b) is conducted in succession or wherein said (b) further comprises changing physical and/or chemical factors in said single aqueous phase after said first primary oil phase or emulsion is dispersed in said single aqueous phase and before said second primary oil phase or emulsion is dispersed in said single aqueous phase.

3. The method of claim 2, wherein said changing is conducted by stirring said single aqueous phase at a speed of from 100 to 5,000 rpm, increasing said aqueous phase to an amount 20 to 1,000 times as large as that of the primary oil phases or emulsions, adding an emulsifier in an amount of 1 to 10% to said single aqueous phase, said emulsifier being selected from the group consisting of polysorbate and polyvinyl alcohol, adding an additive in an amount of 0.1 to 5% to said single aqueous phase, said additive being selected from the group consisting of gelatin, carboxymethylcellulose and calcium, and/or controlling the temperature of said single aqueous phase to be in the range of 5 to 40° C.

4. The method of claim 1, wherein the primary oil phases or emulsions are prepared by a water/oilwater double emulsification process or by an oil/water single emulsification process.

5. The method of claim 1, wherein said biodegradable polymer is selected from the group consisting of polylactide, polyglycolide, poly(lactide-co-glycolide), and mixtures thereof.

6. The method of claim 1, wherein said biodegradable polymer is selected from the group consisting of cellulose acetate, cellulose acetate propionate, cellulose butyrate. cellulose propionate, cellulose valerate, cumaroneindene polymer. dibutylaminohydroxypropyl ether, ethyl cellulose, ethylene-vinyl acetate copolymer. glycerol distearate, hydroxypropylmethyl cellulose phthalate, 2-methyl-5-vinylpyridinc methacrylate-methacrylic acid copolymer, polyamino acids, polyanhydrides polycaprolactone, polycarbonate, polybutadiene, polyesters, polyhydroxybutyric acid polymethyl methacrylate, polymethacrylic acid ester, polyolesters, polypropylene polysaccharides, polystyrene, polyvinyl acetal diethylamino acetate, polyvinyl acetate polyvinyl alcohol, polyvinyl butyral, polyvinyl formal, proteins, vinyl chloride-vinyl acetate polymer, waxes, and higher lipid acids.

7. The method of claim 1, wherein said drug is in a salt form selected from the group consisting of physiologically active peptides and/or proteins, anti-cancer agents, antibiotics, antifebriles, acesodynes, anti-inflammatory agents, expectorants, abirritants, muscle relaxants, epilepsy remedies, anti-ulcerative agents, anti-hypochondriac agents, anti-allergic agents, hypotensive hydragogues, diabetes curatives, hyperlipemie remedies, anticoagulants, hemolytic agents, antituberculous agents, hormones, anesthetic antagonists, osteoclastic suppressants, osteogenic promotives, angiogenesis suppressors, and/mixtures thereof.

8. The method of claim 1, wherein said drug is present in an amount of 1 to 50% in each of the primary oil phases or emulsions and wherein said biodegradable polymer is present in an amount of 5 to 50% in each of the primary oil phases or emulsions.

9. The method of any one of claims 1–7, wherein said drug is selected from the group consisting of goserelin acetate, nafarelin acetate, buserelin acetate, leuprolelin acetate, and mixtures thereof.

10. The method of any one of claims 1–5, wherein said first primary oil phase or emulsion is comprised of a first biodegradable polymer having a weight average molecular weight of 600 to 10,000 and having a lactide:glycolide ranging from 45:55 to 55:45 and wherein said second primary oil phase or emulsion is comprised of a second biodegradable polymer having a weight average molecular weight of 25,000 to 35,000 and having a lactide:glycolide ranging from 45:55 to 55:45; wherein said first and second biodegradable polymers are dispersed in said single aqueous phase to provide microparticles that release said drugs for a prolonged period of time.

11. Sustained release microparticles prepared by the method of claim 1.

* * * * *

UNITED STATES PATENT AND TRADEMARK OFFICE
CERTIFICATE OF CORRECTION

PATENT NO. : 6,506,410 B1
DATED : January 14, 2003
INVENTOR(S) : Park et al.

It is certified that error appears in the above-identified patent and that said Letters Patent is hereby corrected as shown below:

Title page,
Item [75], Inventors, please delete "San Beom Kim" and insert therefore,
-- Sang Beom Kim --.
Item [73], Assignee, please delete "Kong Kook Pharmaceutical Co., Ltd" and insert therefore, -- Dong Kook Pharmaceutical Co., Ltd. --

Column 14,
Line 23, please delete "water/oilwater" and insert therefore, -- water/oil/water --.
Line 37, please delete "vinylpyridinc" and insert therefore, -- vinylpyridine --.
Line 56, please delete "and/mixtures" and insert therefore, -- and mixtures --.

Signed and Sealed this

Eighteenth Day of May, 2004

JON W. DUDAS
*Acting Director of the United States Patent and Trademark Office*